(12) United States Patent
Lee et al.

(10) Patent No.: US 8,298,495 B2
(45) Date of Patent: Oct. 30, 2012

(54) HIGH SENSITIVITY LOCALIZED SURFACE PLASMON RESONANCE SENSOR AND SENSOR SYSTEM USING SAME

(75) Inventors: Kyeong Seok Lee, Seoul (KR); Won Mok Kim, Seoul (KR); Taek Sung Lee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 13/334,113

(22) Filed: Dec. 22, 2011

(65) Prior Publication Data

US 2012/0105857 A1     May 3, 2012

Related U.S. Application Data

(63) Continuation of application No. PCT/KR2009/003576, filed on Jul. 1, 2009.

(51) Int. Cl.
*G01N 33/52*     (2006.01)
*G01N 21/00*     (2006.01)

(52) U.S. Cl. .................................. 422/402; 356/445
(58) Field of Classification Search ........... 356/445–448
See application file for complete search history.

(56) References Cited

U.S. PATENT DOCUMENTS

| | | | | |
|---|---|---|---|---|
| 5,415,842 | A * | 5/1995 | Maule | 422/82.05 |
| 7,648,834 | B2 * | 1/2010 | Moore | 435/287.1 |
| 2004/0048075 | A1 | 3/2004 | Tominaga et al. | |
| 2005/0151973 | A1 | 7/2005 | Naya et al. | |
| 2009/0027668 | A1 | 1/2009 | Fujimaki et al. | |
| 2009/0084166 | A1 * | 4/2009 | Robotti | 73/53.01 |
| 2009/0141376 | A1 | 6/2009 | Smith et al. | |
| 2010/0103495 | A1 * | 4/2010 | Kuang | 359/263 |

FOREIGN PATENT DOCUMENTS

| | | |
|---|---|---|
| JP | 2007-530973 A | 11/2007 |
| JP | 2008-216055 A | 9/2008 |

OTHER PUBLICATIONS

International Search Report issued Mar. 22, 2010 in counterpart International Application No. PCT/KR2009/003576, 9 pages including English translation.

* cited by examiner

*Primary Examiner* — Michael P Stafira
(74) *Attorney, Agent, or Firm* — NSIP Law

(57) ABSTRACT

The present invention relates to a high sensitivity localized surface plasmon resonance sensor and to a sensor system using same, the sensor comprising: a first metal layer including a first metal; a second metal layer arranged parallel to the first metal layer and including a second metal; and a conductive cross-linking layer disposed between the first metal layer and the second metal layer, and made of a third metal with a corrosion response that is different than that of the first metal and of the second metal.

26 Claims, 7 Drawing Sheets

HIGH SENSITIVITY LOCALIZED SURFACE PLASMON RESONANCE SENSOR AND SENSOR SYSTEM USING SAME

CROSS REFERENCE TO RELATED APPLICATION(S)

This application is a continuation of International Patent Application No. PCT/KR2009/003576, filed on Jul. 1, 2009, the entire disclosures of which is incorporated herein by reference for all purposes.

TECHNICAL FIELD

The present disclosure relates to a sensor based on localized surface plasmon resonance occurring in metal nanoparticles or nanostructures. More particularly, the present disclosure relates to a localized surface plasmon resonance sensor using a localized surface plasmon resonance mode generated by a conductive bridge layer formed between nanostructures, and a sensor system using the same.

BACKGROUND ART

A localized surface plasmon refers to a quantized collective motion of free electrons occurring when they are confined in nanometer-sized metal particles or structures. Since the resonance wavelength at which the localized surface plasmon is excited is very sensitively dependent on the size and shape of particles and the change in refractive index of surrounding medium, studies on their applications to biochemical sensors have been extensively carried out.

Unlike a propagating surface plasmon resonance, wherein excitation occurs at the metal/dielectric interface when the condition of both momentum and energy conservation is satisfied in 2-dimensionally confined metal film, the localized surface plasmon resonance occurring in 3-dimensionally confined metallic nanostructures is characterized by a resonant light absorption and a strong scattering accompanied as a results of energy relaxation. The light absorption and scattering can be used as method of spectroscopic signal detection in a sensor application.

Although detection of signals using light absorption is relatively easy, a considerable density of nanostructures is necessary to achieve sufficient light absorption to measure the decreased intensity from a light source. In contrast, detection of signals using light scattering, commonly utilized for imaging of biomolecules and cells, is advantageous in that background noise effect caused by light source can be excluded since only the light signals scattered purely from nanostructures are detected and sensing using single particle is possible. Thus, the signal detection using light scattering facilitates multiplexed detection with high density and avoids the issue of inhomogeneous line broadening of localized surface plasmon resonance spectra resulting from the size and shape distribution.

A localized surface plasmon resonance sensor may be used to detect target molecules with a very small molecular weight and trace amounts of components compared with the surface plasmon resonance sensor whose decay length is hundreds of nanometers or longer since the distribution of local electric field allowing recognition of change in external environment is limited within several to tens of nanometers from the metal nanostructure.

The resolution of the localized surface plasmon resonance sensor is improved as the linewidth of the resonance spectrum is narrower, the intensity of the local electric field near the metal nanostructure is stronger, and the sensitivity to change in external environment represented by the change in resonance wavelength in response to the change in the refractive index of the surrounding material is higher.

In general, as the shape of the metal nanostructure changes from spherical to ellipsoidal, the surface plasmon resonance wavelength shifts toward longer wavelength, the intensity of the local electric field increases, and the sensitivity to external change is enhanced. Among the ellipsoidal structures, prolate structure is more favorable for use in a sensor than plate-shaped oblate structure.

A similar phenomenon is observed when the size of the nanostructure is increased. As the size increases, the localized surface plasmon resonance wavelength shows redshift, the intensity of the local electric field increases, and the sensitivity to external change is enhanced. However, in this case, the collective motion of free electrons in the particles becomes incoherent, resulting in multipole modes and damping of surface plasmon, which excessively increase the linewidth of resonant optical absorption or scattering curves and thus the resolution of the sensor is decreased.

Typically, the metal nanostructure is prepared as colloidal particles in solutions by chemical or electrochemical synthesis method or fabricated on a specific support substrate by a lithographic process. When compared with the solution-based synthesis wherein reaction kinetics are adjusted during particle nucleation and growth, the lithographic process is advantageous in that it is easy to realize various geometrical structures, precise control of shape and size is possible, and it is well adopted for the fabrication of array of nanoparticles and sensor integration.

Figure 1:
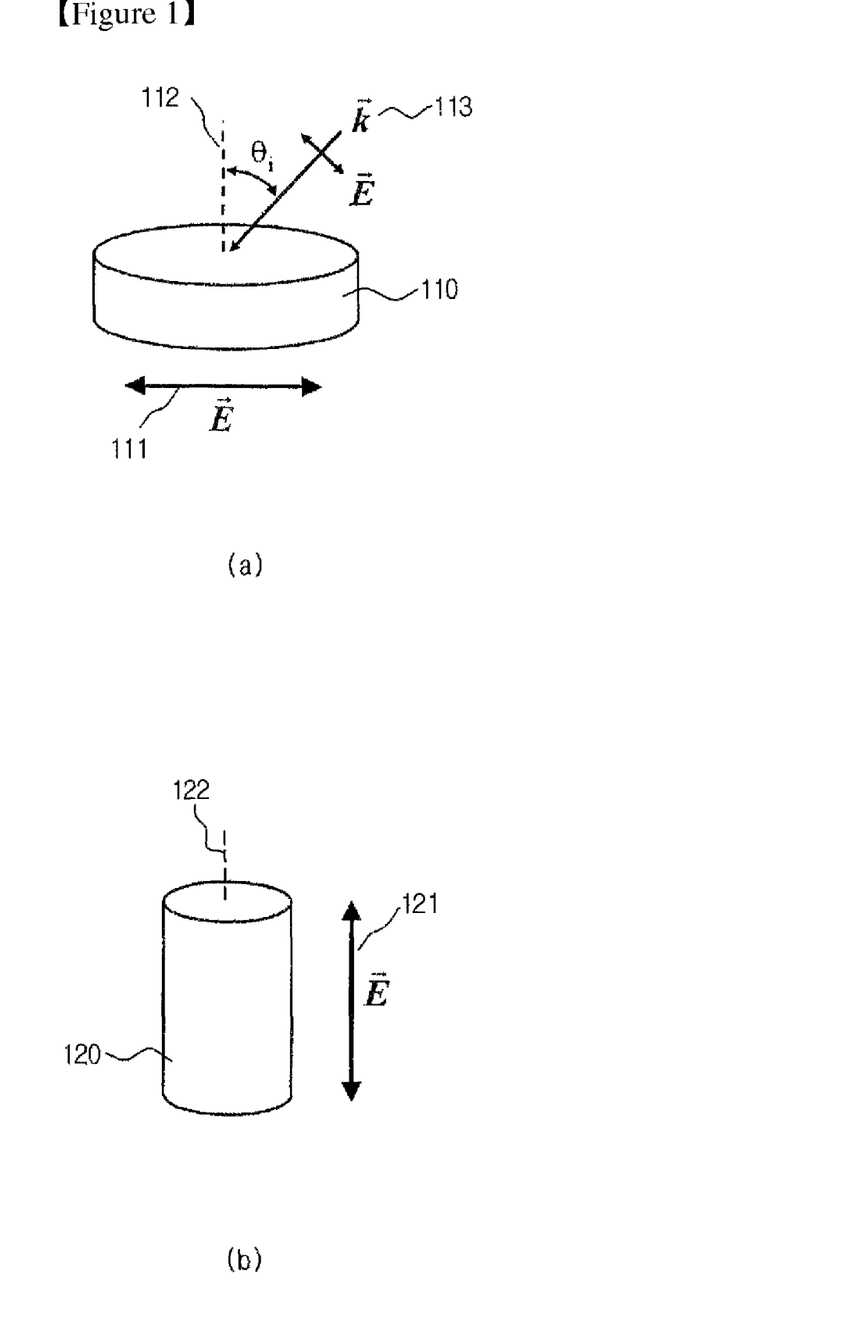
FIG. 1 shows a conventional type of sensing platforms of metal nanostructure based on localized surface plasmon resonance.

FIG. 1 illustrates a conventional type of sensing platforms of metal nanostructure based on localized surface plasmon resonance.

FIGS. 1 (a) and (b) show basic sensing platforms used in fabrication of nanostructures by a lithographic process. FIG. 1 (a) shows a cylindrical plate-type nanodisc platform 110, and FIG. 1 (b) shows a cylindrical nanorod platform 120.

The plate-type nanodisc platform 110 has an oblate structure, with the electric field direction 111 of the incident light perpendicular to the axis of rotation 112. Although the lithographic process for the plate-type nanodisc is easier as compared to the nanorod type platform 120, the intensity of local electric field and sensitivity are relatively worse. In contrast, the nanorod type platform 120 exhibits superior plasmonic resonance properties in longitudinal mode when the electric field direction 121 of the incident light is parallel to the long axis 122, but the increase in aspect ratio for improving the intensity of local electric field and sensitivity results in difficulty in the lithographic process because of reduced width in the short axis. To increase the length in the long axis without decreasing the width in the short axis is undesirable since the total volume is increased inducing a line broadening. Furthermore, the increased aspect ratio results in the reduction in cross-section of end surface of nanorod where the local electric field enhancement due to the excitation of longitudinal mode of surface plasmon is concentrated, leading to unfavorable environment for detection of thin analytes positioned on that surfaces. A similar problem occurs also in the oblate-type nanodisc platform 110. In the plate-type nanodisc platform 110, the intensity of local electric field and sensitivity are increased when the electric field direction 111 of the incident light is perpendicular to the axis of rotation 112 and as the thickness-to-area ratio of the disc increases. However the local electric field is concentrated at the edge of the disc rather than the surface region where the major portion of analytes are positioned on through surface functionalization, deteriorating the sensing resolution.

Also, the plate-type nanodisc platform 110 and the nanorod type platform 120 have problems when light scattering is used for single particle detection. Typically, the spectroscopic scattering properties are analyzed using a dark-field microscope or a total internal reflection microscope. Referring to FIG. 1 (a), in dark field microscopy, light 113 is incident on the surface of a sample to be analyzed with an incidence angle $\theta_i$ from a direction 112 normal to the surface, and only the diffuse scattering components excluding the specular components are detected. The incidence angle $\theta_i$ makes the electric field be divided into two components: one is perpendicular and the other is parallel to the sample surface, diminishing the portion of component for optimized localized surface plasmon.

In analysis using total internal reflection microscopy, both S and P waves can be used. And, since the evanescent electric field formed at the interface of total reflection is either perpendicular or parallel to the sample, the problem of electric field division which occurs in the dark field microscopy can be avoided.

DISCLOSURE

Technical Problem

The present disclosure is directed to providing a highly sensitive localized surface plasmon resonance sensor based on a plate-type nanodisc structure easily fabricated by the lithographic process, with an enhanced intensity of local electric field, reduced line width of optical absorption and scattering spectra, and improved sensitivity to the change in external environment comparable to or better than that of the longitudinal mode of a nanorod, and a sensor system using the same.

Technical Solution

A localized surface plasmon resonance sensor according to an embodiment includes: a first metal layer including a first metal; a second metal layer arranged parallel to the first metal layer and including a second metal; and a conductive bridge layer disposed between the first metal layer and the second metal layer and including a third metal with a corrosion reactivity different from that of the first metal and the second metal.

The conductive bridge layer may have a diameter smaller than that of the first metal layer and the second metal layer.

A localized surface plasmon resonance sensor system according to an embodiment includes: a localized surface plasmon resonance sensor including a first metal layer including a first metal, a second metal layer arranged parallel to the first metal layer and including a second metal, and a conductive bridge layer disposed between the first metal layer and the second metal layer and including a third metal with a corrosion reactivity different from that of the first metal and the second metal; a light transmitter transmitting an incident light; and a light detector detecting a light absorption signal and a light scattering signal for the incident light from the light transmitter according to the characteristics of the localized surface plasmon resonance sensor.

Advantageous Effects

The localized surface plasmon resonance sensor according to embodiments is advantageous in that the lithographic process is facile and, since a nanodisc-type structure with a relatively large plate surface is used and a localized surface plasmon resonance mode of the longitudinal mode characteristics can be excited by forming a vertical conductive bridge, the intensity of local electric field applied on the plate surface of nanodisc is increased. Furthermore, the line width of the light absorption and scattering spectra accompanying resonance can be reduced and the resolution of the sensor can be enhanced by remarkably improving the sensitivity to change in external environment. Also, by using an evanescent field optimized for the excitation of localized surface plasmon mode from the vertical conductive bridge layer, the convenience of sensor configuration as well as sensor chip integration and operation reliability can be enhanced.

MODE FOR INVENTION

Hereinafter, exemplary embodiments will be described in detail with reference to the accompanying drawings.

Figure 2:
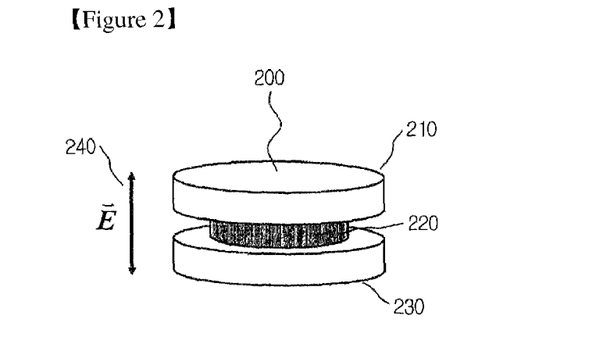
FIG. 2 shows a metal nanostructure for a localized surface plasmon resonance sensor according to an embodiment.

FIG. 2 shows a metal nanostructure of a localized surface plasmon resonance sensor according to an embodiment.

Referring to FIG. 2, a nanostructure 200 of a localized surface plasmon resonance sensor according to an embodiment comprises a first metal layer 210, a conductive bridge layer 220 and a second metal layer 230.

The first metal layer 210 and the second metal layer 230 are arranged such that the plate surfaces thereof are parallel to each other. The first metal layer 210 and the second metal layer 230 may be in the form of a plate-type nanodisc. Also, the first metal layer 210 and the second metal layer 230 may have a planar structure and may have various shapes including circular, elliptical, polygonal, annular, etc. as well as various thicknesses. The second metal layer 230 may be a 2-dimensional metal film.

The first metal layer 210 comprises a first metal, and the second metal layer 230 comprises a second metal. The first metal or the second metal may be one or more noble metal selected from Au, Ag, Cu, etc., which exhibit localized surface plasmon resonance in the visible and near infrared regions with low absorptive loss by the metal itself, or an alloy comprising the one or more metal. The first metal and the second metal may be the same or different metals.

The conductive bridge layer 220 is disposed between the first metal layer and the second metal layer. Specifically, the both end-surfaces of the conductive bridge layer 220 are connected to the bottom of the first metal layer 210 and the top of the second metal layer 230, respectively. And, the conductive bridge layer 220 comprises a third metal. The third metal has different corrosion reactivity from the first metal and the second metal. The corrosion reactivity may include oxidation, nitration and fluoridation as well as etching properties. And, the corrosion reactivity of the third metal may be higher or distinctive as compared to the corrosion reactivity of the first metal and the second metal. Since the third metal has different corrosion reactivity from the first metal and the second metal, the properties of localized surface plasmon resonance sensor may be controlled by oxidizing or etching the nanostructure 200. The conductive bridge 220 may be given a smaller diameter than the first metal layer 210 and the second metal layer 230 via a selected oxidation or etching process. The resonance characteristics of the sensor may also be varied by adjusting the diameter or length of the conductive bridge 220.

The third metal may comprise one or more metal selected from Cu, Ag, Au, Sn, Al, Pt and Ti, which exhibit high electrical conductivity, low optical loss and superior selective etching property or good oxidation or nitration reactivity, or an alloy comprising the one or more metal.

In the localized surface plasmon resonance sensor according to an embodiment, the excitation of longitudinal mode type localized surface plasmons due to the conductive bridge 220 may be achieved by applying an incident light such that the direction of an electric field 240 thereof is parallel to the conductive bridge 220 and perpendicular to the plate surfaces of the first metal layer 210 and the second metal layer 230.

Figure 3:
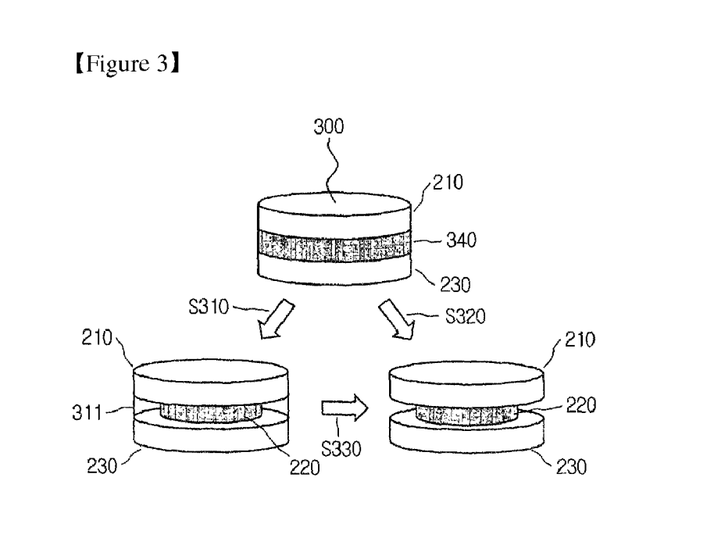
FIG. 3 schematically shows a process of fabricating a localized surface plasmon resonance sensor and sensing platforms according to an embodiment.

FIG. 3 schematically shows a process of fabricating a localized surface plasmon resonance sensor and sensing platforms according to an embodiment.

Referring to FIG. 3, a nanostructure of a localized surface plasmon resonance sensor according to an embodiment may be fabricated from a multilayered plate-type nanodisc structure 300 via an oxidation process S310 or an etching process S320.

First, a multilayered plate-type nanodisc structure 300 is fabricated by inserting an intermediate layer 340 comprising a third metal having different corrosion reactivity between a first metal layer 210 and a second metal layer 230. The nanodisc structure may be fabricated using various lithographic processes. For example, the lithographic process may include an etching process or a lift-off process. The etching process may involve deposition of a 3-layer metal film on a substrate with predetermined thickness, formation of polystyrene beads or e-beam resist layer as etching mask and etching such as reactive ion etching (RIE) for fabrication of the plate-type nanodisc. The lift-off may involve formation of a cylindrical nanotemplate layer with sufficient thickness using an e-beam resist, anodized aluminum, a block copolymer, etc., deposition of a metal film thereon and removal of the template for fabrication of the plate-type nanodisc.

When the fabrication of the plate-type nanodisc structure 300 is completed, the oxidation/nitration process S310 or the etching process S320 may be selectively proceeded depending on the characteristics of the intermediate layer 340 so as to form a conductive bridge 220 with a decreased diameter. When the oxidation process S310 is carried out on the intermediate layer 340, oxidation occurs from the outer portion of the intermediate layer 340, resulting in an outer perimetric oxide layer 311 divided from the inner conductive bridge 220. The oxidation process may be replaced by a nitration process depending on the material characteristics of the intermediate layer 340. It is beneficial that the produced oxide or nitride is a transparent material passing light therethrough in the wavelength region where localized surface plasmons are formed. The outer perimetric oxide layer of the intermediate layer 340 may be left unremoved or may be removed by a subsequent etching process S330.

Figure 4:
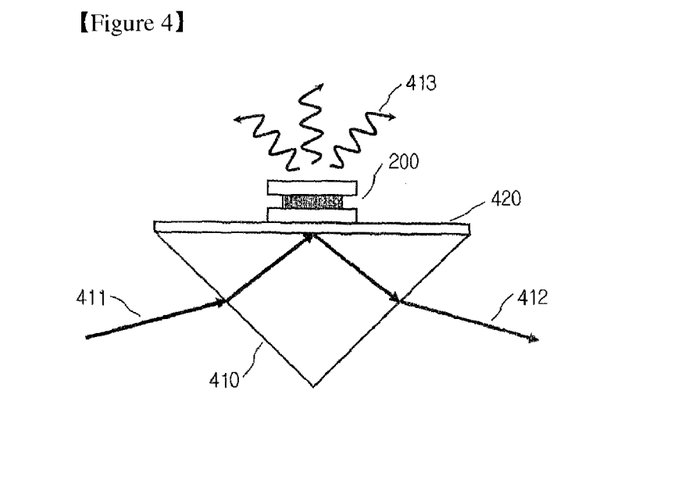
FIG. 4 is a longitudinal cross-sectional view of a localized surface plasmon resonance sensor comprising a prism according to another embodiment.

FIG. 4 is a longitudinal cross-sectional view of a localized surface plasmon resonance sensor comprising a prism according to another embodiment.

Referring to FIG. 4, a localized surface plasmon resonance sensor according to another embodiment comprises a nanostructure 200 according to the above-described embodiment, a prism 410 and a dielectric buffer layer or interface adhesion layer 420.

The prism 410 is connected to the bottom of the second metal layer. Specifically, the bottom surface of the prism 410 is connected to the bottom of the second metal layer of the nanostructure 200 to transmit light energy. The prism 410 may totally reflect a light incident from any one of surfaces at its basal plane and excite a localized surface plasmon mode in the length direction of the conductive bridge layer of the nanostructure using an evanescent field generated due to the total internal reflection at the basal plane. The prism 410 may be a rectangular prism, a cylindrical prism having a hemispherical cross section, a trapezoidal prism, or the like.

The prism 410 may be connected to the nanostructure 200 either directly or via the dielectric buffer layer 420 or the interfacial adhesion layer 420 inserted between the second metal layer and the prism 410. The interfacial adhesion layer 420 may comprise a transparent conducting oxide such as indium tin oxide (ITO) or one or more material selected from Ti, W, Cr, TiN, $Ta_2O_5$ and ZnS—$SiO_2$, and various materials may be used depending on applications.

An incident light 411 is P-wave polarized so that the electric field component of the evanescent field generated on the basal plane of the prism 410 is dominant in a direction perpendicular to the basal plane of the prism. The localized surface plasmons excited by the evanescent field in the nanostructure 200 either absorb the incident light 411 or re-emit it as a scattered light 413.

The signal detection by the sensor may be achieved either by observing the change in the intensity of a reflected light 412 due to the light absorption caused by the localized surface plasmon resonance or by measuring the spectrum of the scattered light 413.

Figure 5:
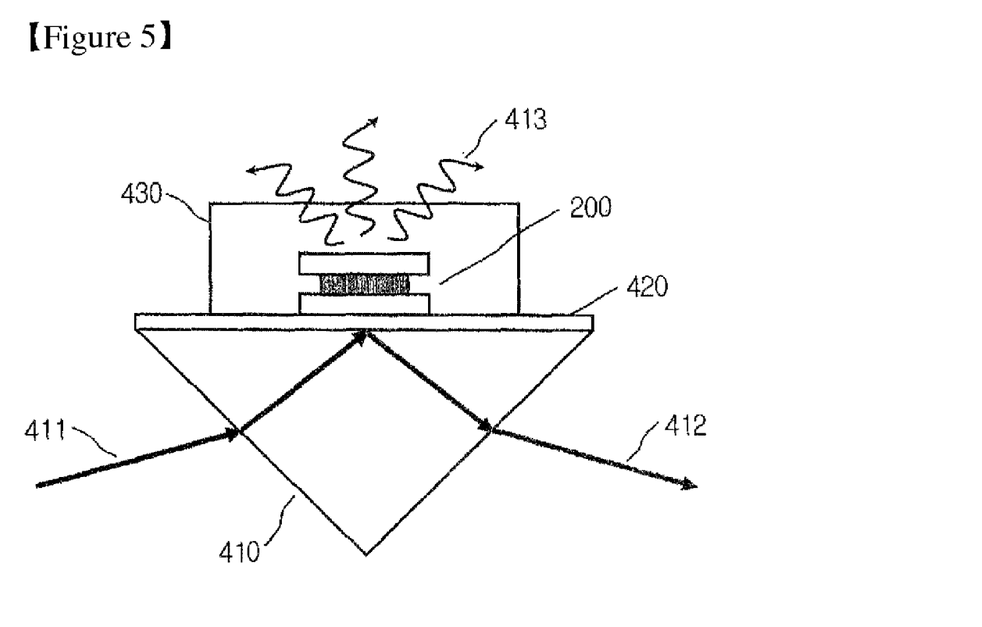
FIG. 5 shows a longitudinal cross-sectional view of a localized surface plasmon resonance sensor comprising an additional sensing layer for detection of external environment according to another embodiment.

FIG. 5 shows a longitudinal cross-sectional view of a localized surface plasmon resonance sensor comprising an additional sensing layer for detection of external environment according to another embodiment.

Referring to FIG. 5, a localized surface plasmon resonance sensor according to another embodiment further comprises an sensing layer 430 in addition to the plasmon resonance sensor according to the embodiment described referring to FIG. 4.

The external environment sensing layer 430 changes optical properties such as refractive index sensitively in response to the change in external environment. The external environment sensing layer 430 may comprise a material whose optical properties change sensitively responding in chemical gas or liquid, including metal oxides, organic-polymer materials, chalcogenide materials, semiconductor materials, etc. It is desirable that the sensing layer comprises a transparent material passing light therethrough at the operation wavelength in order to prevent the surface plasmon damping. The external environment sensing layer 430 may enclose the nanostructure 200 comprising the first metal layer, the conductive bridge layer and the second metal layer.

Figure 6:
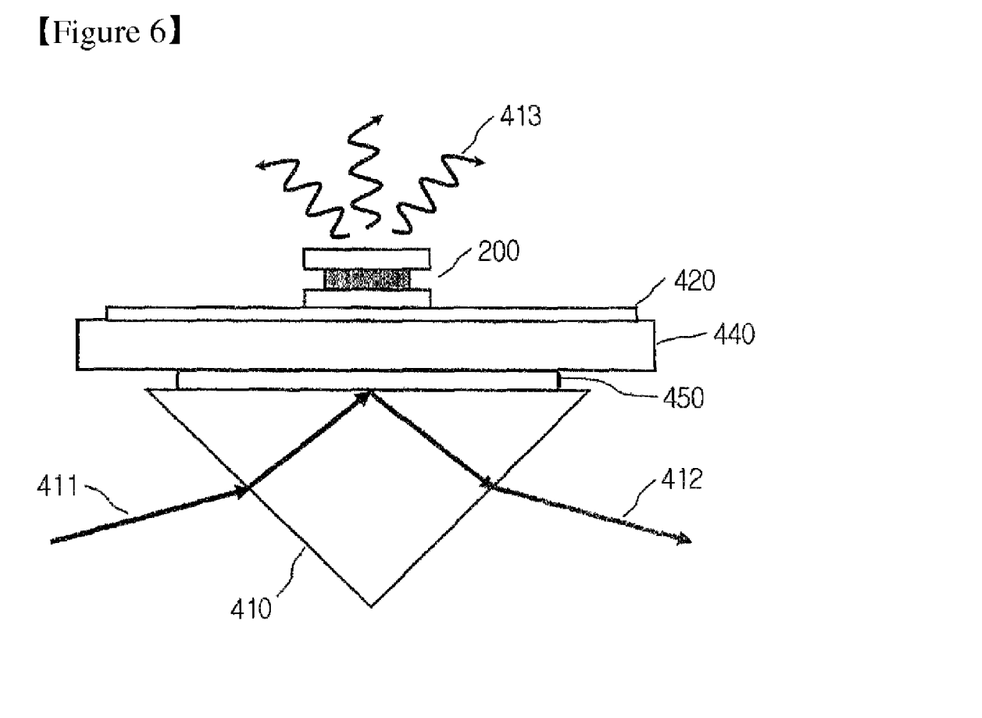
FIG. 6 shows a longitudinal cross-sectional view of a localized surface plasmon resonance sensor comprising a plate-type substrate according to another embodiment.

FIG. 6 shows a longitudinal cross-sectional view of a localized surface plasmon resonance sensor comprising a plate-type substrate according to another embodiment.

Referring to FIG. 6, a localized surface plasmon resonance sensor according to another embodiment further comprises a plate-type substrate 440 and an index-matching oil layer 450 in addition to the plasmon resonance sensor according to the embodiment described referring to FIG. 4.

The plate-type substrate 440 may comprise a material optically transparent at the operation wavelength, either organic or inorganic, including soda-lime glass, borosilicate glass, fused silica glass, etc. The introduction of the plate-type substrate 440 allows application of various etching processes for fabrication of the nanostructure 200. Further, the plate-type substrate 440 may allow easy control of the process for improving film quality when forming the dielectric buffer layer or the interfacial adhesion layer 420 which positioned on the bottom of the nanostructure 200.

The upper surface of the plate-type substrate 440 may be connected to the nanostructure 200 either directly or via a dielectric buffer layer 420 or an interfacial adhesion layer 420. The interface adhesion layer 420 may comprise a transparent conducting oxide such as ITO or one or more material selected from Ti, W, Cr, TiN, $Ta_2O_5$ and ZnS—$SiO_2$, and various materials may be used depending on applications.

An index-matching oil layer 450 may be inserted between the plate-type substrate 440 and the prism 410. The index-matching oil layer 450 acts to optically couple the plate-type substrate 440 to the prism 410.

Figure 7:
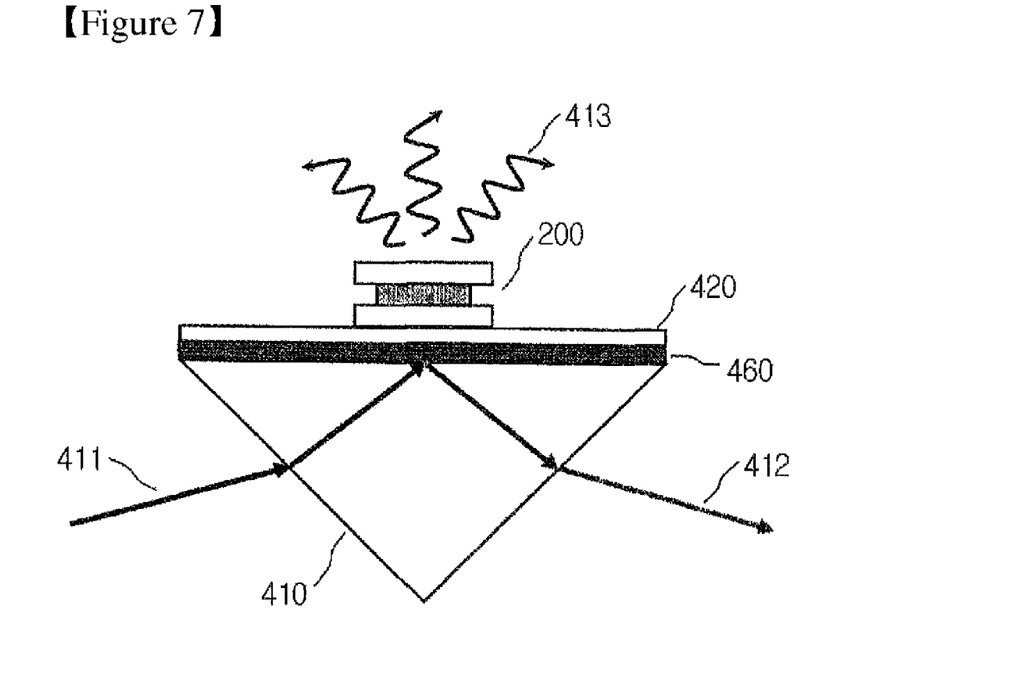
FIG. 7 shows a longitudinal cross-sectional view of a localized surface plasmon resonance sensor comprising a layer of exciting a propagating surface plasmon according to another embodiment.

FIG. 7 shows a longitudinal cross-sectional view of a localized surface plasmon resonance sensor comprising a layer of exciting a propagating surface plasmon according to another embodiment.

Referring to FIG. 7, a localized surface plasmon resonance sensor according to another embodiment further comprises a layer of exciting a propagating surface plasmon 460 in addition to the localized surface plasmon resonance sensor according to the embodiment described referring to FIG. 4.

The layer of exciting propagating surface plasmon 460 may enhance the intensity of local electric field at the interface of the prism 410 and enhance the intensity of light absorption and light scattering by localized surface plasmon resonance, by exciting surface plasmon polaritons near the basal plane of the prism 410.

The layer of exciting propagating surface plasmon 460 may be a metal layer comprising one or more metal selected from Au, Ag and Cu or an alloy material comprising the one or more metal. Also, in order to maximize the local electric field enhancement effect, the layer of exciting propagating surface plasmon may comprises a dielectric/metal/dielectric sandwich-type structure, wherein a upper and a lower dielectric layers and a metal layer inserted between them are disposed, capable of exciting long-range surface plasmon. In addition, the layer of exciting propagating surface plasmon may comprises a waveguide-coupled surface plasmon resonance layer consisting of a upper and a lower metal layers, and a dielectric waveguide layer inserted between them is also possible.

Figure 8:
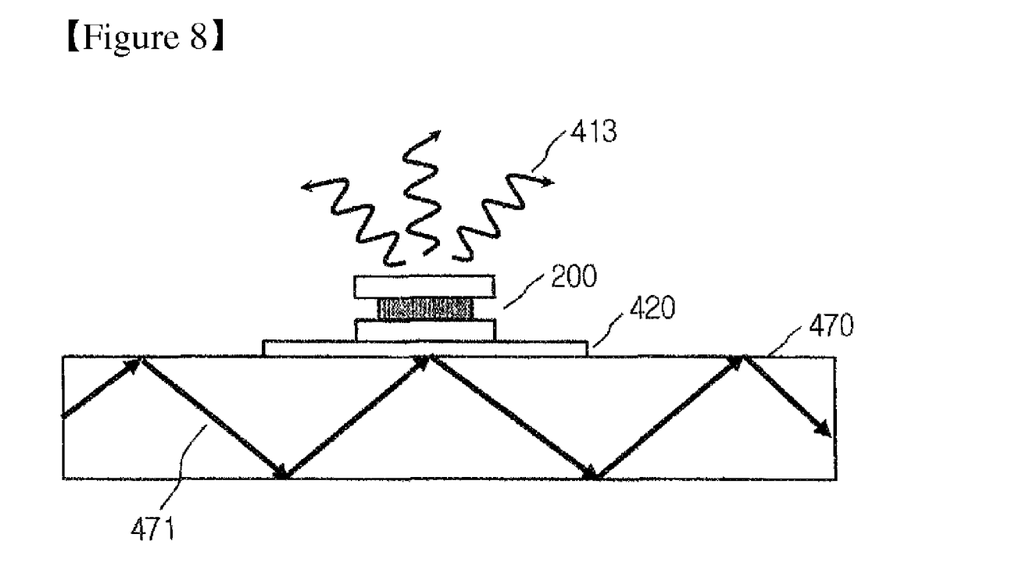
FIG. 8 shows a longitudinal cross-sectional view of a localized surface plasmon resonance sensor comprising an optical waveguide layer according to another embodiment.

FIG. 8 shows a longitudinal cross-sectional view of a localized surface plasmon resonance sensor comprising an optical waveguide layer according to another embodiment.

Referring to FIG. 8, a localized surface plasmon resonance sensor according to another embodiment comprises the above-described nanostructure 200 according to an embodiment and an optical waveguide layer 470.

The optical waveguide layer 470 generates an evanescent field due to a guided wave mode 471 propagating through an optical waveguide and thus excites localized surface plasmons. The optical waveguide layer 470 may be an optical fiber or an integrated optical waveguide, without particular limitation. The optical waveguide layer 470 may be connected to the nanostructure 200 either directly or via a dielectric buffer layer 420 or an interfacial adhesion layer 420. The interfacial adhesion layer 420 may comprise a transparent conducting oxide such as ITO or one or more material selected from Ti, W, Cr, TiN, $Ta_2O_5$ and ZnS—$SiO_2$, and various materials may be used depending on applications.

By using the optical waveguide layer 470 as a light source transmitter and a part of exciting surface plasmons, an integrated sensor or a sensor array chip can be easily fabricated. Also, when an optical fiber is used as the optical waveguide layer 470, remote monitoring is possible by analyzing the change in the intensity and spectrum of guided wave 471. The light incident to the optical waveguide needs to be in a TM mode so as to form an evanescent field in a direction perpendicular to the interface of the localized surface plasmon resonance sensor.

A localized surface plasmon sensor system according to an embodiment comprises: the localized surface plasmon resonance sensor according to an embodiment; a light transmitter transmitting an incident light; and a light detector detecting a light absorption signal and a light scattering signal for the incident light from the light transmitter according to the characteristics of the localized surface plasmon resonance sensor. For spectroscopic analysis, the incident light may be white light. Even when monochromatic light is used, the change in signal intensity at the resonance wavelength in response to the change in external environment may be detected.

In addition, a metal nanostructure of the localized surface plasmon resonance sensor according to the present disclosure may be used as a basic platform for surface enhanced Raman spectroscopy.

Figure 9:
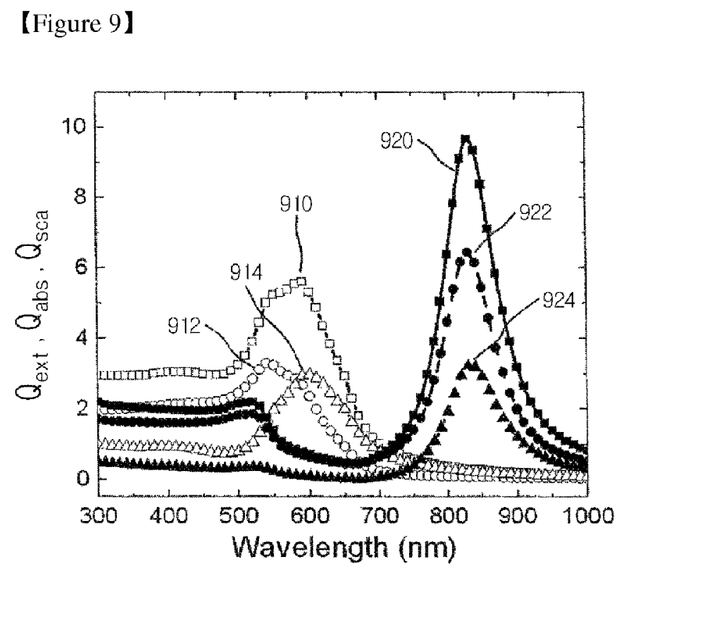
FIG. 9 compares spectra of efficiencies of optical extinction, absorption, and scattering of a localized surface plasmon resonance sensor according to an embodiment before and after formation of a conductive bridge.

FIG. 9 compares total extinction efficiency (920), light absorption efficiency (922) and scattering efficiency (924) spectra of a localized surface plasmon resonance sensor according to an embodiment with those (910, 912, 914) before the formation of a conductive bridge.

Referring to FIG. 9, a localized surface plasmon resonance sensor according to an embodiment comprises Au nanodiscs having a diameter of 100 nm and a length of 20 nm as a first metal layer and a second metal layer, and a Cu nanodisc having a diameter of 60 nm and a length of 20 nm as a conductive bridge. The light absorption and scattering characteristics of the nanostructure were calculated by a computer simulation based on discrete dipole approximation (DDA) method for the case where the electric field direction of incident light is perpendicular to the plate surface of the nanodisc. As seen from FIG. 9, before the conductive bridge is formed, the extinction efficiency (910), absorption efficiency (912) and scattering efficiency (914) spectra due to localized surface plasmon resonance exhibits simply a combination of the transverse modes of the Au and Cu nanodiscs. However, as the diameter of the intermediate Cu layer is decreased and the conductive bridge is formed, the localized surface plasmon resonance wavelength red-shifts, and the absolute intensity of the extinction efficiency (920), absorption efficiency (922) and scattering efficiency (924) increases. Also, the linewidth of the spectra is decreased and the spectra become sharper. These characteristics are very similar to the longitudinal mode characteristics observed in the nanorod structure and can be further controlled by varying the material of the bridge layer and the geometrical structure.

Figure 10:
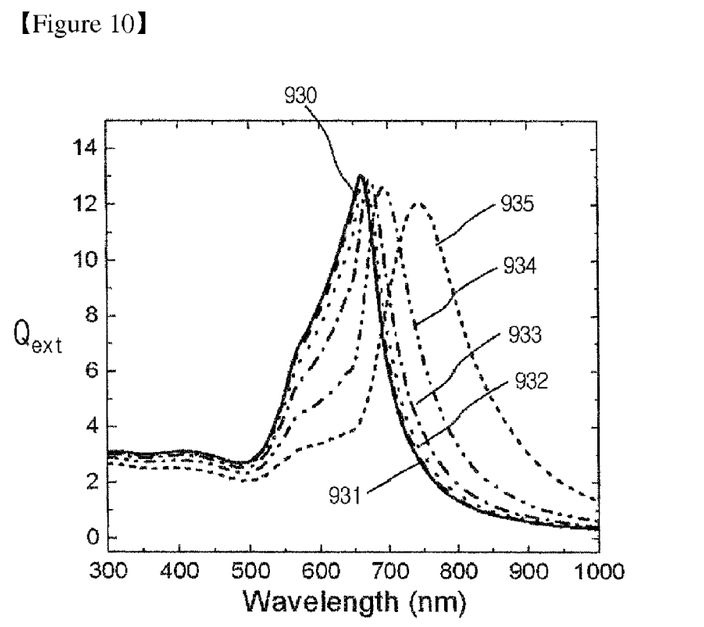
FIG. 10 shows extinction efficiency spectra of a conventional single Au nanodisc having an oblate structure in response to change in the refractive index of surrounding medium.
Figure 11:
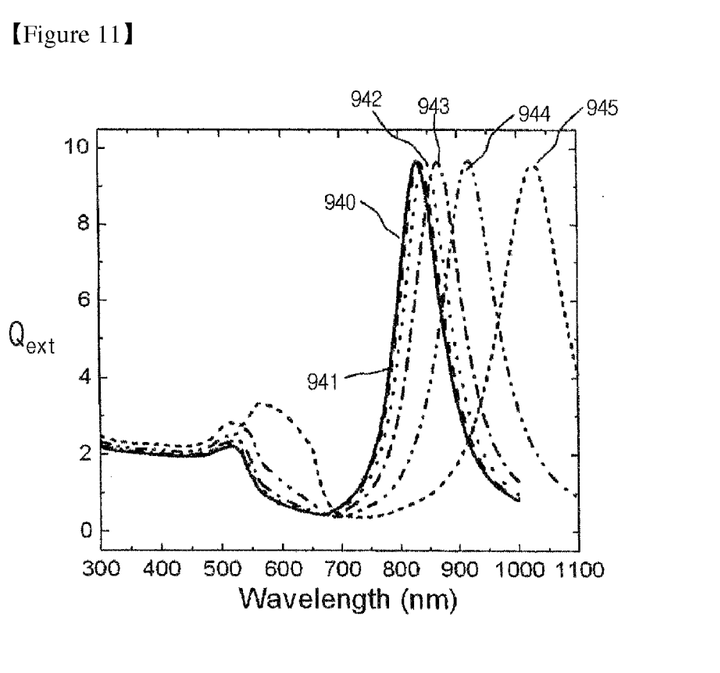
FIG. 11 shows extinction efficiency spectra of a localized surface plasmon resonance sensor according to an embodiment in response to change in the refractive index of surrounding medium.
Figure 12:
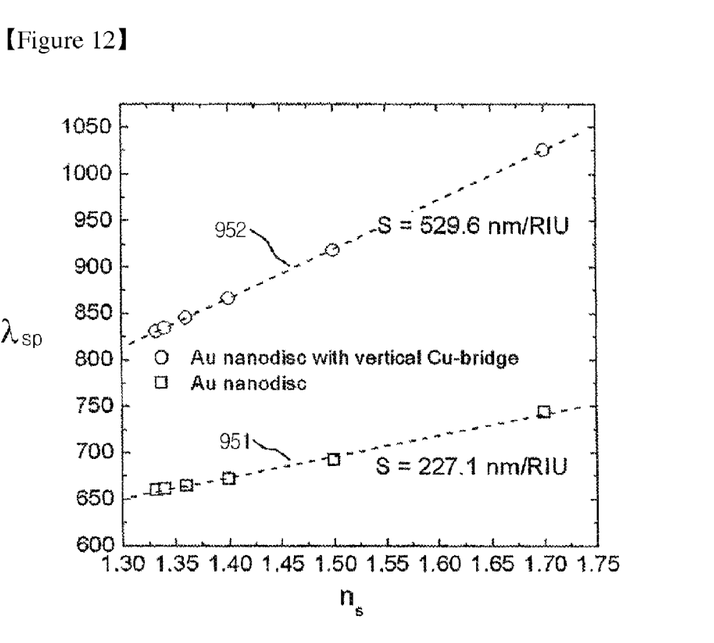
FIG. 12 shows changes in resonance wavelength in response to change in the refractive index of surrounding medium of a conventional single Au nanodisc having a oblate structure and a localized surface plasmon resonance sensor according to an embodiment.

FIGS. 10 to 12 show results of comparing with a conventional single Au nanodisc for evaluation of enhancement of sensitivity to change in external environment by a localized surface plasmon resonance sensor according to an embodiment.

FIG. 10 shows the spectra of extinction efficiency for a conventional single Au nanodisc having a plate-type oblate structure in response to change in the refractive index of surrounding medium.

FIG. 10 shows a result of calculation based on the assumption that the electric field direction of incident light is perpendicular to the rotational axis so that the localized surface plasmon resonance properties are optimized. The diameter and thickness of Au nanodisc are 100 nm and 50 nm, respectively. It was assumed that the refractive index of the surrounding medium changes gradually from an initial refractive index of 1.332 (930) to 1.34 (931), 1.36 (932), 1.4 (933), 1.5 (934) and 1.7 (935), and the extinction efficiency spectra of the Au nanodisc were computationally simulated. As the refractive index of the surrounding medium was increased, the surface plasmon resonance wavelength exhibited red shift.

FIG. 11 shows extinction efficiency spectra of a localized surface plasmon resonance sensor according to an embodiment in response to change in the refractive index of surrounding medium.

FIG. 11 shows a result based on the assumption that the refractive index of the surrounding medium changes gradually from 1.332 (940) to 1.34 (941), 1.36 (942), 1.4 (943), 1.5 (944) and 1.7 (945), as in FIG. 10, and the extinction efficiency spectra were computationally simulated. When comparing with FIG. 10, the red-shift of the resonance wavelength in response to the change of the refractive index of the surrounding medium was remarkable and the linewidth of the extinction efficiency spectra was narrower in FIG. 11, which imply the enhanced resolution.

FIG. 12 summarizes the quantitative change in resonance wavelength in response to change in the refractive index of surrounding medium for both a conventional single Au nanodisc (951) having a plate-type oblate structure and a localized surface plasmon resonance sensor (952) according to an embodiment.

Referring to FIG. 12, both cases (951, 952) show a linear red-shift in the surface plasmon resonance wavelength as the refractive index of the surrounding medium increases. In FIG. 12, the change in resonance wavelength in response to the refractive index of the surrounding medium representing the sensitivity of the sensor can be determined from the slope of the respective lines. The nanostructure (952) having a vertical conductive bridge according to an embodiment exhibited a sensitivity of 529.6 nm/RIU, more than 2 times larger than 227.1 nm/RIU of the Au nanodisc (951) without a conductive bridge.

The resonance characteristics and sensitivity of the localized surface plasmon resonance sensor according to embodiments may be further controlled by changing the geometrical structure and material of the first metal layer, the second metal layer and the conductive bridge layer.

Figure 13:
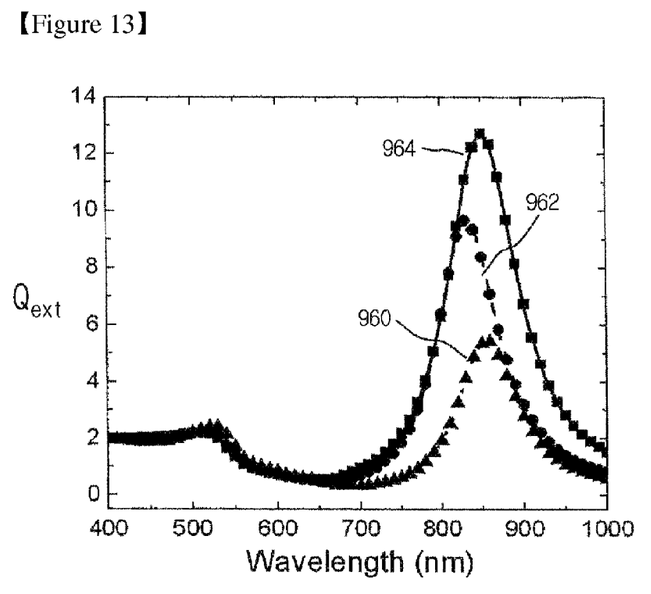
FIG. 13 shows change in extinction efficiency spectra of a localized surface plasmon resonance sensor according to an embodiment in response to increased length of a conductive bridge layer.

FIG. 13 shows change in extinction efficiency spectra of a localized surface plasmon resonance sensor according to an embodiment in response to increased length of a conductive bridge. The same basic structure as that of the localized surface plasmon resonance sensor shown in FIG. 9 was used, and the length of the Cu conductive bridge was changed from 10 nm (960) to 20 nm (962) and 30 nm (964).

Referring to FIG. 13, it can be seen that the extinction efficiency is greatly enhanced as the length of the Cu conductive bridge is increased. When the length of the conductive bridge is 10 nm (960), the resonance wavelength is observed in a longer wavelength as compared to when the length of the conductive bridge is 20 nm (962) due to the dipole interaction between neighboring Au nanodiscs. And, as the length of conductive bridge is increases larger than 20 nm, the gradual red-shift in resonance wavelength is observed very similar to that of the longitudinal mode of a nanorod. In addition to the change of the extinction efficiency, the relative ratio of the absorption efficiency to the scattering efficiency may also increases as the length of the conductive bridge is increased.

The change in the diameter as well as the length of the conductive bridge also has an important effect on the characteristics of localized surface plasmon resonance. In general, as the diameter of the conductive bridge decreases, the red-shift of localized surface plasmon resonance wavelength become significant, the extinction efficiency increases and the relative ratio of the scattering efficiency increases.

Figure 14:
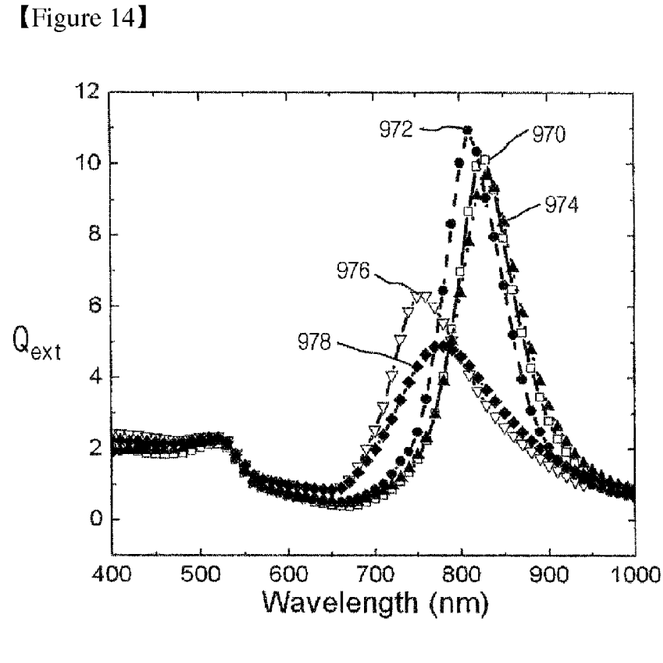
FIG. 14 shows the dependence of extinction efficiency spectra of a localized surface plasmon resonance sensor according to an embodiment on the selection of materials for the conductive bridge layer.

FIG. 14 shows change in extinction efficiency spectra of a localized surface plasmon resonance sensor according to an embodiment in dependent on materials selection for the conductive bridge. The structure of the localized surface plasmon resonance sensor was the same as that of FIG. 9, and Au (970), Ag (972), Cu (974), Al (976) or Sn (978) were used as the conductive bridge materials.

Referring to FIG. 14, when Al (976) or Sn (978) was used, the linewidth of the extinction efficiency curve was broadened and the intensity decreased because of surface plasmon damping caused by absorption of material itself as compared to when the noble metals Au (970), Ag (972) or Cu (974) were used. Such problems can be complemented by adjusting the geometry of the nanostructure or using the noble metal exhibiting superior plasmonic properties, such as Ag, in the lower metal layer.

The localized surface plasmon resonance sensor according to the present disclosure provides a longitudinal mode type surface plasmon resonance generated due to a conductive bridge. In addition, the hot-spot effect of electric field concentrated in the nanogap formed near the conductive bridge allows further improvement of sensitivity when the target molecules and analytes exist there.

INDUSTRIAL APPLICABILITY

The present disclosure is applicable to a biochemical sensor utilizing localized surface plasmon resonance characteristics occurring from metal nanoparticles or nanostructures.

The invention claimed is:

1. A localized surface plasmon resonance sensor comprising:
  a first metal layer comprising a first metal;
  a second metal layer arranged parallel to the first metal layer and comprising a second metal; and
  a conductive bridge layer disposed between the first metal layer and the second metal layer and comprising a third metal with a corrosion reactivity different from that of the first metal and the second metal,
  wherein the first metal and the second metal are either one or more metal selected from a group consisting of Au, Ag and Cu or an alloy comprising the one or more metal, and the first metal is same as or different from the second metal.

2. The localized surface plasmon resonance sensor according to claim 1, wherein the conductive bridge layer has a diameter smaller than that of the first metal layer and the second metal layer.

3. The localized surface plasmon resonance sensor according to claim 1, wherein the third metal is one or more metal selected from a group consisting of Cu, Ag, Au, Sn, Al, Pt and Ti or an alloy comprising the one or more metal.

4. The localized surface plasmon resonance sensor according to claim 1, wherein the first metal layer or the second metal layer has a plate-type structure.

5. The localized surface plasmon resonance sensor according to claim 1, wherein the second metal layer is a 2-dimensional metal film.

6. The localized surface plasmon resonance sensor according to claim 1, wherein the length or diameter of the conductive bridge layer is adjusted to control the plasmonic resonance properties of the sensor.

7. The localized surface plasmon resonance sensor according to claim 1, which further comprises a prism connected to the bottom of the second metal layer and totally reflecting an incident light.

8. The localized surface plasmon resonance sensor according to claim 7, which further comprises a dielectric buffer layer or an interfacial adhesion layer between the second metal layer and the prism, wherein the interfacial adhesion layer comprises a transparent conducting oxide or one or more material selected from a group consisting of Ti, W, Cr, TiN, $Ta_2O_5$ and $ZnS-SiO_2$.

9. The localized surface plasmon resonance sensor according to claim 7, which further comprises an external environment sensing layer enclosing the first metal layer, the conductive bridge layer and the second metal layer, wherein a refractive index of the external environment sensing layer is changed in response to a change in external environment.

10. The localized surface plasmon resonance sensor according to claim 8, wherein the external environment sensing layer comprises a transparent material passing light therethrough.

11. The localized surface plasmon resonance sensor according to claim 7, which further comprises a plate-type substrate between the second metal layer and the prism.

12. The localized surface plasmon resonance sensor according to claim 11, wherein the plate-type substrate is made of a transparent material passing light therethrough.

13. The localized surface plasmon resonance sensor according to claim 11, which further comprises an index-matching oil layer disposed between the plate-type substrate and the prism and optically coupling the plate-type substrate, with the prism.

14. The localized surface plasmon resonance sensor according to claim 11, which further comprises a dielectric buffer layer or an interfacial adhesion layer between the second metal layer and the plate-type substrate, wherein the interfacial adhesion layer comprises a transparent conducting oxide or one or more material selected from a group consisting of Ti, W, Cr, TiN, $Ta_2O_5$ and $ZnS-SiO_2$.

15. The localized surface plasmon resonance sensor according to claim 7, which further comprises a layer of exciting propagating surface plasmon disposed between the second metal layer and the prism and exciting surface plasmon polaritons.

16. The localized surface plasmon resonance sensor according to claim 15, wherein the layer of exciting propagating surface plasmon comprises one or more metal selected from a group consisting of Au, Ag and Cu or an alloy comprising the one or more metal.

17. The localized surface plasmon resonance sensor according to claim 15, wherein the layer of exciting propagating surface plasmon comprises a dielectric upper layer, a metal layer connected to the dielectric upper layer and a dielectric lower layer connected to the metal layer.

18. The localized surface plasmon resonance sensor according to claim 15, wherein the layer of exciting propagating surface plasmon comprises a metal upper layer, a dielectric waveguide layer connected to the metal upper layer and a metal lower layer connected to the dielectric waveguide layer.

19. The localized surface plasmon resonance sensor according to claim 1, which further comprises an optical waveguide layer connected to the bottom of the second metal layer.

20. The localized surface plasmon resonance sensor according to claim 19, which further comprises a dielectric buffer layer or an interfacial adhesion layer between the second metal layer and the optical waveguide layer, wherein the interfacial adhesion layer comprises a transparent conducting oxide or one or more material selected from a group consisting of Ti, W, Cr, TiN, $Ta_2O_5$ and $ZnS-SiO_2$.

21. A localized surface plasmon resonance sensor system comprising:
  the localized surface plasmon resonance sensor according to claim 1;
  a light transmitter transmitting an incident light; and
  a light detector detecting a light absorption signal and a light scattering signal for the incident light from the light transmitter according to the characteristics of the localized surface plasmon resonance sensor.

22. The localized surface plasmon resonance sensor according to claim 1, wherein a first end-surface of the conductive bridge layer contacts the first metal layer, and a second end-surface of the conductive bridge layer contacts the second metal layer.

23. The localized surface plasmon resonance sensor according to claim 1, wherein the first metal layer and the second metal layer are a nanodisc.

24. A localized surface plasmon resonance sensor comprising:
a first metal layer comprising a first metal;
a second metal layer arranged parallel to the first metal layer and comprising a second metal; and
a conductive bridge layer disposed between the first metal layer and the second metal layer and comprising a third metal with a corrosion reactivity different from that of the first metal and the second metal,
wherein the first metal layer, the second metal layer and the conductive bridge layer together form a nanostructure.

25. The localized surface plasmon resonance sensor according to claim 24, wherein the first metal layer and the second metal layer are an Au nanodisc, and the conductive bridge layer is a nano disc of a third metal having a higher corrosion reactivity than that of the first and the second metal.

26. The localized surface plasmon resonance sensor according to claim 25, wherein a first end-surface of the conductive bridge layer contacts the first metal layer, and a second end-surface of the conductive bridge layer contacts the second metal layer.

* * * * *